(12) United States Patent
Ortiz et al.

(10) Patent No.: US 9,463,264 B2
(45) Date of Patent: Oct. 11, 2016

(54) BONE GRAFTS AND METHODS OF MAKING AND USING BONE GRAFTS

(71) Applicant: GLOBUS MEDICAL, INC, Audubon, PA (US)

(72) Inventors: Ophir Ortiz, Philadelphia, PA (US); Archana Bhat, Royersford, PA (US); Allison Adams, Philadelphia, PA (US); Mark Adams, Downingtown, PA (US)

(73) Assignee: Globus Medical, Inc., Audubon, PA (US)

( * ) Notice: Subject to any disclaimer, the term of this patent is extended or adjusted under 35 U.S.C. 154(b) by 206 days.

(21) Appl. No.: 14/177,967

(22) Filed: Feb. 11, 2014

(65) Prior Publication Data

US 2015/0223937 A1 Aug. 13, 2015

(51) Int. Cl.
*A61F 2/28* (2006.01)
*A61L 27/46* (2006.01)

(52) U.S. Cl.
CPC ............ *A61L 27/46* (2013.01); *A61F 2240/00* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 4,437,191 A | 3/1984 | van der Zel et al. | |
| 5,231,169 A | 7/1993 | Constantz et al. | |
| 5,681,872 A | 10/1997 | Erbe | |
| 5,700,289 A | 12/1997 | Breitbart et al. | |
| 5,776,193 A | 7/1998 | Kwan et al. | |
| 5,854,207 A | 12/1998 | Lee et al. | |
| 5,914,356 A | 6/1999 | Erbe | |
| 5,939,039 A | 8/1999 | Sapieszko et al. | |
| 6,123,731 A | 9/2000 | Boyce et al. | |
| 6,264,701 B1 | 7/2001 | Brekke | |
| 6,294,041 B1 | 9/2001 | Boyce et al. | |
| 6,309,659 B1 | 10/2001 | Clokie | |
| 6,350,283 B1 | 2/2002 | Michelson | |
| 6,372,257 B1 | 4/2002 | Marchosky | |
| 6,432,436 B1 | 8/2002 | Gertzman et al. | |
| 6,437,018 B1 | 8/2002 | Gertzman et al. | |
| 6,666,890 B2 | 12/2003 | Michelson | |
| 6,696,073 B2 | 2/2004 | Boyce et al. | |
| 6,706,067 B2 | 3/2004 | Shimp et al. | |
| 6,723,131 B2 | 4/2004 | Muschler | |
| 6,749,636 B2 | 6/2004 | Michelson | |
| 6,752,831 B2 | 6/2004 | Sybert et al. | |
| 6,776,800 B2 | 8/2004 | Boyer, II et al. | |
| 6,808,585 B2 | 10/2004 | Boyce et al. | |
| 6,843,807 B1 | 1/2005 | Boyce et al. | |
| 6,919,308 B2 | 7/2005 | Oppermann et al. | |
| 6,949,251 B2 | 9/2005 | Dalal et al. | |
| 7,022,137 B2 | 4/2006 | Michelson | |
| 7,041,641 B2 | 5/2006 | Rueger et al. | |
| 7,132,110 B2 | 11/2006 | Kay et al. | |
| 7,156,880 B2 | 1/2007 | Evans et al. | |
| 7,166,133 B2 | 1/2007 | Evans et al. | |
| 7,175,858 B2 | 2/2007 | Constantz et al. | |
| 7,235,107 B2 | 6/2007 | Evans et al. | |
| 7,262,003 B2 | 8/2007 | Kumar et al. | |
| 7,275,933 B2 | 10/2007 | Jia et al. | |
| 7,291,345 B2 | 11/2007 | Winterbottom et al. | |
| 7,332,452 B2 | 2/2008 | Ogawa et al. | |
| 7,381,224 B1* | 6/2008 | Li | A61L 27/46 623/23.51 |
| 7,390,498 B2 | 6/2008 | Dalal et al. | |
| 7,393,405 B2 | 7/2008 | Bohner | |
| 7,473,678 B2 | 1/2009 | Lynch | |
| 7,494,950 B2 | 2/2009 | Armitage et al. | |
| 7,498,041 B2 | 3/2009 | Masinaei et al. | |
| 7,517,489 B2 | 4/2009 | Akash | |
| 7,582,309 B2 | 9/2009 | Rosenberg et al. | |
| 7,611,536 B2 | 11/2009 | Michelson | |
| 7,723,395 B2 | 5/2010 | Ringeisen et al. | |
| 7,744,597 B2 | 6/2010 | Gaskins et al. | |
| 7,776,100 B2 | 8/2010 | Brekke et al. | |
| 7,785,634 B2 | 8/2010 | Borden | |
| 7,811,608 B2 | 10/2010 | Kay et al. | |
| 7,824,702 B2 | 11/2010 | Wironen et al. | |
| 7,833,278 B2 | 11/2010 | Evans et al. | |
| 7,887,598 B2 | 2/2011 | Evans et al. | |
| 7,892,291 B2 | 2/2011 | Evans et al. | |
| 7,910,690 B2 | 3/2011 | Ringeisen et al. | |
| 7,931,692 B2 | 4/2011 | Sybert et al. | |
| 7,939,108 B2 | 5/2011 | Morris et al. | |
| 7,942,961 B2 | 5/2011 | Asgarg | |
| 7,947,759 B2 | 5/2011 | Lin et al. | |
| 7,959,941 B2 | 6/2011 | Knaack et al. | |
| 7,977,094 B2 | 7/2011 | Masinaei et al. | |
| 8,002,813 B2 | 8/2011 | Scarborough et al. | |
| 8,067,078 B1 | 11/2011 | Espinosa et al. | |
| 8,093,313 B2 | 1/2012 | Miller | |
| 8,105,383 B2 | 1/2012 | Michelson | |
| 8,137,403 B2 | 3/2012 | Michelson | |
| 8,147,860 B2 | 4/2012 | Rosenberg et al. | |
| 8,147,862 B2 | 4/2012 | McKay | |
| 8,163,032 B2 | 4/2012 | Evans et al. | |
| 8,188,229 B2 | 5/2012 | Ringeisen et al. | |
| 8,197,474 B2 | 6/2012 | Scarborough et al. | |

(Continued)

FOREIGN PATENT DOCUMENTS

| | | |
|---|---|---|
| CA | 1341610 C | 4/1989 |
| CA | 2027259 C | 12/2000 |
| WO | 2005084701 A1 | 9/2005 |
| WO | 2014128289 A1 | 8/2014 |

*Primary Examiner* — Robert Yamasaki

(57) ABSTRACT

Provided herein are bone grafts and methods of making and using the same, as well as products and kits that include such bone grafts. In particular, bone grafts are provided that include collagen Type I and one or more different types of mineral compositions having different dissolution properties and/or sizes, to enhance bone regeneration throughout the bone healing phase.

16 Claims, 1 Drawing Sheet

(56) References Cited

U.S. PATENT DOCUMENTS

| | | |
|---|---|---|
| 8,202,539 B2 | 6/2012 | Behnam et al. |
| 8,221,781 B2 | 7/2012 | Rosenberg et al. |
| 8,232,327 B2 | 7/2012 | Garigapati et al. |
| 8,268,008 B2 | 9/2012 | Betz et al. |
| 8,287,915 B2 | 10/2012 | Clineff et al. |
| 8,303,967 B2 | 11/2012 | Clineff et al. |
| 8,303,971 B2 | 11/2012 | Cieslik et al. |
| 8,309,106 B2 | 11/2012 | Masinaei et al. |
| 8,323,700 B2 | 12/2012 | Morris et al. |
| 8,328,876 B2 | 12/2012 | Behnam et al. |
| 8,333,985 B2 | 12/2012 | Knaack et al. |
| 8,357,384 B2 | 1/2013 | Behnam et al. |
| 8,394,141 B2 | 3/2013 | Mills et al. |
| 8,399,409 B2 | 3/2013 | Lynch et al. |
| 8,419,802 B2 | 4/2013 | Evans et al. |
| 8,425,619 B2 | 4/2013 | Evans et al. |
| 8,435,306 B2 | 5/2013 | Evans et al. |
| 8,435,343 B2 | 5/2013 | Yahav et al. |
| 8,435,566 B2 | 5/2013 | Behnam et al. |
| 8,454,988 B2 | 6/2013 | Rosenberg et al. |
| 8,460,686 B2 | 6/2013 | Clineff et al. |
| 8,475,824 B2 | 7/2013 | McKay |
| 8,506,981 B1 | 8/2013 | Borden |
| 8,506,985 B2 | 8/2013 | Garcia De Castro Andrews et al. |
| 8,524,265 B2 | 9/2013 | McKay |
| 8,529,962 B2 | 9/2013 | Morris et al. |
| 8,545,858 B2 | 10/2013 | Rosenberg et al. |
| 8,545,864 B2 | 10/2013 | Morris et al. |
| 8,551,519 B2 | 10/2013 | Bezwada |
| 8,551,525 B2 | 10/2013 | Cook et al. |
| 8,562,648 B2 | 10/2013 | Kaes et al. |
| 8,580,865 B2 | 11/2013 | Peters et al. |
| 8,597,675 B2 | 12/2013 | Murphy et al. |
| 8,613,938 B2 | 12/2013 | Akella et al. |
| 8,623,094 B2 | 1/2014 | Evans et al. |
| 8,641,774 B2 | 2/2014 | Rahaman et al. |
| 8,642,061 B2 | 2/2014 | Shimp et al. |
| 8,652,503 B2 | 2/2014 | Wironen et al. |
| 8,663,326 B2 | 3/2014 | Osman |
| 8,663,672 B2 | 3/2014 | Manrique et al. |
| 8,663,677 B2 | 3/2014 | Fu et al. |
| 8,685,429 B2 | 4/2014 | Koblish et al. |
| 8,734,525 B2 | 5/2014 | Behnam et al. |
| 8,740,987 B2 | 6/2014 | Geremakis et al. |
| 8,747,899 B2 | 6/2014 | Chaput et al. |
| 8,753,391 B2 | 6/2014 | Lu et al. |
| 8,753,689 B2 | 6/2014 | Morris et al. |
| 8,758,792 B2 | 6/2014 | Behnam et al. |
| 8,778,378 B2 | 7/2014 | Clineff et al. |
| 8,795,382 B2 | 8/2014 | Lin et al. |
| 8,802,626 B2 | 8/2014 | Rueger et al. |
| 8,834,928 B1 | 9/2014 | Truncale et al. |
| 8,864,843 B2 | 10/2014 | Lu et al. |
| 8,871,235 B2 | 10/2014 | Borden |
| 8,876,532 B2 | 11/2014 | Atkinson et al. |
| 8,877,221 B2 | 11/2014 | McKay |
| 8,883,210 B1 | 11/2014 | Truncale et al. |
| 8,926,710 B2 | 1/2015 | McKay |
| 8,992,964 B2 | 3/2015 | Shelby et al. |
| 8,992,965 B2 | 3/2015 | Behnam |
| 2001/0038848 A1 | 11/2001 | Donda et al. |
| 2002/0076429 A1 | 6/2002 | Wironen et al. |
| 2002/0098222 A1 | 7/2002 | Wironen et al. |
| 2002/0193883 A1 | 12/2002 | Wironen |
| 2003/0009235 A1 | 1/2003 | Manrique et al. |
| 2003/0055512 A1 | 3/2003 | Genin et al. |
| 2003/0149437 A1 | 8/2003 | Livne et al. |
| 2004/0091462 A1 | 5/2004 | Lin et al. |
| 2005/0118230 A1 | 6/2005 | Hill et al. |
| 2005/0251267 A1 | 11/2005 | Winterbottom et al. |
| 2005/0281856 A1 | 12/2005 | McGlohorn et al. |
| 2006/0018942 A1 | 1/2006 | Rowe et al. |
| 2006/0036331 A1 | 2/2006 | Lu et al. |
| 2006/0147545 A1 | 7/2006 | Scarborough et al. |
| 2007/0083270 A1 | 4/2007 | Masinaei et al. |
| 2007/0098756 A1 | 5/2007 | Behnam |
| 2007/0105222 A1 | 5/2007 | Wolfinbarger et al. |
| 2007/0113951 A1 | 5/2007 | Huang |
| 2008/0033572 A1 | 2/2008 | D'Antonio et al. |
| 2008/0069852 A1 | 3/2008 | Shimp et al. |
| 2008/0091270 A1 | 4/2008 | Miller et al. |
| 2008/0152687 A1 | 6/2008 | Thorne |
| 2008/0187571 A1 | 8/2008 | Clineff et al. |
| 2009/0012625 A1 | 1/2009 | Ying et al. |
| 2009/0074753 A1 | 3/2009 | Lynch |
| 2009/0157087 A1 | 6/2009 | Wei et al. |
| 2009/0192474 A1 | 7/2009 | Wei et al. |
| 2009/0312842 A1 | 12/2009 | Bursac et al. |
| 2009/0317447 A1 | 12/2009 | Hsiao et al. |
| 2010/0055078 A1 | 3/2010 | Hughes-Fulford |
| 2010/0098673 A1 | 4/2010 | D'Antonio et al. |
| 2010/0145469 A1 | 6/2010 | Barralet et al. |
| 2010/0196333 A1 | 8/2010 | Gaskins et al. |
| 2010/0203155 A1 | 8/2010 | Wei et al. |
| 2010/0234966 A1 | 9/2010 | Lo |
| 2011/0045044 A1 | 2/2011 | Masinaei et al. |
| 2011/0066242 A1 | 3/2011 | Lu et al. |
| 2011/0070312 A1 | 3/2011 | Wei et al. |
| 2011/0117018 A1 | 5/2011 | Hart et al. |
| 2011/0117165 A1 | 5/2011 | Melican et al. |
| 2011/0117166 A1 | 5/2011 | Melican |
| 2011/0117171 A1 | 5/2011 | Melican et al. |
| 2011/0144764 A1 | 6/2011 | Bagga et al. |
| 2011/0224675 A1 | 9/2011 | Tofighi et al. |
| 2011/0262554 A1 | 10/2011 | Masinaei et al. |
| 2011/0276147 A1 | 11/2011 | Cook et al. |
| 2011/0280924 A1 | 11/2011 | Lin et al. |
| 2012/0053692 A1 | 3/2012 | Voor et al. |
| 2012/0064290 A1 | 3/2012 | Esat et al. |
| 2012/0093895 A1 | 4/2012 | Song et al. |
| 2012/0164187 A1 | 6/2012 | Ollila et al. |
| 2012/0207839 A1 | 8/2012 | Liu et al. |
| 2012/0237568 A1 | 9/2012 | Murphy et al. |
| 2013/0013071 A1 | 1/2013 | Betz et al. |
| 2013/0059382 A1 | 3/2013 | Tsai et al. |
| 2013/0122057 A1 | 5/2013 | Garigapati et al. |
| 2013/0144376 A1 | 6/2013 | Dave et al. |
| 2013/0145963 A1 | 6/2013 | Cai et al. |
| 2013/0150227 A1 | 6/2013 | Wang et al. |
| 2013/0189338 A1 | 7/2013 | Drapeau et al. |
| 2013/0195805 A1 | 8/2013 | Wei et al. |
| 2013/0202670 A1 | 8/2013 | Darmac et al. |
| 2013/0236513 A1 | 9/2013 | Guelcher et al. |
| 2013/0244942 A1 | 9/2013 | Benedict et al. |
| 2013/0274890 A1 | 10/2013 | McKay |
| 2013/0282138 A1 | 10/2013 | McKay |
| 2013/0297038 A1 | 11/2013 | McKay |
| 2014/0031950 A1 | 1/2014 | Cook et al. |
| 2014/0079753 A1 | 3/2014 | Darby et al. |
| 2014/0170202 A1 | 6/2014 | Peters et al. |
| 2014/0195005 A1 | 7/2014 | McKay |
| 2014/0205674 A1 | 7/2014 | Wei |
| 2014/0212471 A1 | 7/2014 | Drapeau et al. |
| 2014/0222159 A1 | 8/2014 | Bursac et al. |
| 2014/0271779 A1 | 9/2014 | Bagga et al. |
| 2014/0271786 A1 | 9/2014 | Bagga et al. |
| 2014/0271914 A1 | 9/2014 | Wagner |
| 2014/0294913 A1 | 10/2014 | Hasirci et al. |
| 2014/0314822 A1 | 10/2014 | Carter et al. |
| 2015/0010607 A1 | 1/2015 | Francis et al. |

\* cited by examiner

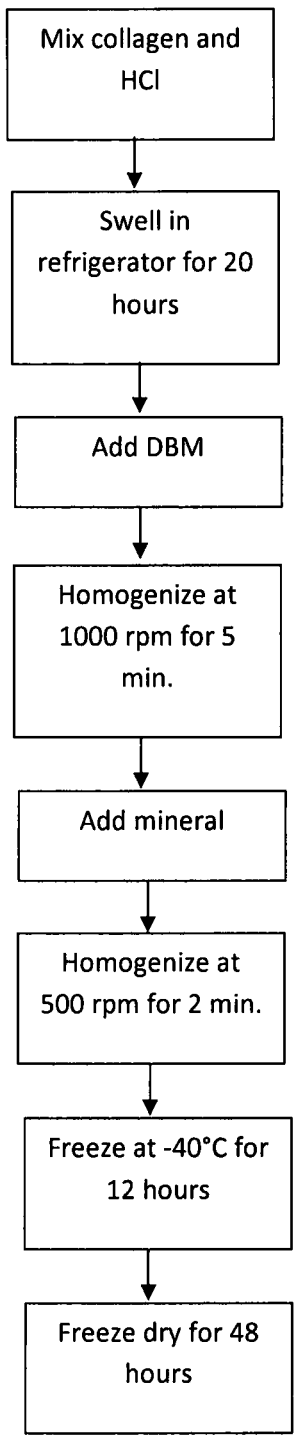

BONE GRAFTS AND METHODS OF MAKING AND USING BONE GRAFTS

FIELD OF THE INVENTION

The present invention generally relates to bone grafts, and methods of making and using the same. The invention also relates to bone grafts that include collagen Type I and one or more different types of minerals having different dissolution properties, and/or one or more sizes. Further included are kits and implants having the present bone grafts; and methods of making and using the present bone grafts.

BACKGROUND

Bone generally has the ability to regenerate completely, e.g., after a fracture but requires a very small fracture space or some sort of scaffold to do so. Bone grafting is a surgical procedure that replaces missing bone to repair bone fractures that are very complex, fail to heal properly, or pose a significant health risk to the patient.

Bone grafts may be autologous (bone harvested from the patient's own body, often from the iliac crest), allograft (cadaveric bone usually obtained from a bone bank), or synthetic (often made of hydroxyapatite or other naturally occurring and biocompatible substances) with similar mechanical properties to bone. Most bone grafts are expected to be reabsorbed and replaced as the natural bone heals over a few months' time.

Bone grafts are osteogenic if they contain viable cells that are capable of bone regeneration. The current gold standard in bone graft substitutes for spine and long bone applications is autograft (i.e., using the patient's own tissue), followed by allografts. Autografts are considered osteogenic, as they contain a high number of bone forming cells. However, autographs may have limited availability and they are limited by donor site morbidity. Also, autografts may require multiple surgeries. Allografts are limited by the large variability in performance due to source and processing steps.

There is a need to produce superior bone grafts that are osteogenic and/or are able to enhance bone regeneration throughout the bone healing phase.

SUMMARY

According to non-limiting example embodiments, the present invention provides bone grafts that include collagen and one or more minerals having different dissolution properties or rates and/or sizes, to enhance bone regeneration throughout the bone healing phase. These minerals can be, for example, in the form of a calcium phosphate, carbonate apatite, and/or calcium carbonate.

Other example embodiments are directed to methods for preparing the bone grafts provided herein. Further example embodiments are directed to methods that include administering a bone graft substitute to a mammal by surgically inserting one or more of the present bone grafts into a mammal. The bone grafts may be administered for example by themselves e.g., in the form of a strip, putty, gel and sponge, or the bone graft may be available in conjunction with an implant, such as being incorporated therein or thereon.

Yet further example embodiments are directed to implants or other devices that include one more of the bone grafts provided herein therein or thereon. Other example embodiments are directed to kits that include one or more of the present bone grafts and/or components or ingredients that may be combined mixed or treated to prepare the present bone grafts, as well as instructions, devices, implants, tools or other components that may assist with making or using the present bone grafts.

BRIEF DESCRIPTION OF DRAWINGS

Non-limiting example embodiments are described herein, with reference to the following accompanying FIGURE:

FIG. 1 is a flow chart of an example method of preparing a bone graft according to non-limiting examples of the present invention.

DETAILED DESCRIPTION OF THE INVENTION

The present invention is drawn to bone grafts and methods for making and using such bone grafts, as well as kits and implants or other devices including the same.

While the example embodiments are described to be used in conjunction with healing bone fractures, it should be understood that these bone grafts may be used for other purposes and therefore the present invention is not limited to such applications. In view of the teachings provided herein, one having ordinary skill in the art would recognize other applications for which the bone grafts of the present invention could be used, and would be able to use the bone grafts and methods of the present invention in other applications. Accordingly, these alternative uses are intended to be part of the present invention.

Additional aspects, advantages and/or other features of example embodiments of the invention will become apparent in view of the following detailed description, taken in conjunction with the accompanying drawings. It should be apparent to those skilled in the art that the described embodiments provided herein are merely exemplary and illustrative and not limiting. Numerous embodiments of modifications thereof are contemplated as falling within the scope of this disclosure and equivalents thereto.

In describing example embodiments, specific terminology is employed for the sake of clarity. However, the embodiments are not intended to be limited to this specific terminology. Unless otherwise noted, technical terms are used according to conventional usage.

As used herein, "a" or "an" may mean one or more. As used herein "another" may mean at least a second or more. Furthermore, unless otherwise required by context, singular terms include pluralities and plural terms include the singular.

As used herein, the term "mammal" is intended to include any "subject" or "patient" animal, (including, but not limited to humans) to whom the present bone grafts may be administered. A subject or patient or mammal may or may not be under current medical care, and may or may not have had one or more prior treatments. As would be apparent to those skilled in the art, the formulations may be different for non-humans than for humans.

As used herein, "an effective amount" refers to an amount of the specified constituent in a composition or formulation, or an amount of the overall formulation that is effective in attaining results, the purpose for which the constituent or composition is provided. Therefore, an effective amount of a bone graft formulation would be an amount suitable for achieving the desired bone graft effect in a subject, such as a mammal (e.g., human) to which the present bone graft is administered.

Numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

According to non-limiting example embodiments, bone grafts may be prepared that include collagen and one or more minerals, including but not limited to calcium phosphates, carbonate apatite, and/or calcium carbonate having both "fast" and "slow" dissolution rates. The "fast" or "faster" dissolution rates help bone healing in the early phases (from e.g., weeks up to a couple of months after the bone graft has been implanted into a patient), while the minerals having slower dissolution rates can be present for e.g., up to two years in the patient after implantation. The terms fast and slow are relative terms, but are meant to be relative with respect to each other, and the relative rates would be apparent to those skilled in the art in the context of the present disclosure in the bone grafting context. That is, a skilled practitioner would be able to determine which minerals may have faster or slower dissolution rates that may be appropriate in the bone grafting context for dissolution at a desired rate.

Therefore, a goal of the present invention is to produce a bone graft that circumvents limitations of prior bone grafts by: (1) regenerating bone without the need to harvest bone from the patient; (2) having a bone regenerating material with lower variability in osteogenic properties relative to allograft; and (3) including mineral (e.g., calcium phosphate, carbonate apatite, and/or calcium carbonate), with or without the optional ingredients of demineralized bone matrix (DBM), and with or without hyaluronic acid. The incorporation of more than one mineral will provide a range of dissolution rates, which will allow for the bone graft to enhance bone healing in both early and late phases of bone healing.

These embodiments of the present bone grafts will thus, be an alternative to the use of autografts and allografts. These embodiments will also be an alternative to currently available collagen-based bone grafts because they will have minerals incorporated, which will have one or more dissolution rates to enhance bone healing in both early and late stages.

Minerals differing in dissolution rate and/or size can be used in the present bone grafts. The possible combinations of minerals in these embodiments will interact with new bone formation throughout the bone healing process. For instance, if two or more minerals are chosen, then one mineral will be active in the early bone healing, and the second mineral will be active in the later stage of bone healing. According to alternative embodiments, a third or more mineral having yet a different dissolution rate and/or size can be incorporated.

An additional benefit of the present bone grafts in relation to the different sizes and/or dissolution rates of the minerals, is that the mineral with the "slow" dissolution rate may also have a porous structure. This porous structure will help in the entrapment of growth factors and/or osteoprogenitor cells, which literature has suggested as being the mechanism for osteoinduction in calcium phosphate-based materials.

Thus, according to non-limiting example embodiments, the present invention provides bone grafts that include collagen type I and at least one, two, or more different types of minerals, such as calcium phosphates, carbonate apatites, and/or calcium carbonates, having different dissolution properties/rates and/or different sizes than one another, to enhance bone regeneration throughout the bone healing phase.

According to non-limiting example embodiments, bone grafts are provided which include: 20% to 95% by weight (with respect to the final product) of Collagen Type I and 20% to 95% by weight (with respect to the final product) of minerals having different dissolution properties and/or sizes than one another. According to example embodiments, the minerals may include one or more minerals selected from calcium phosphates, carbonate apatites, and/or calcium carbonates, According to example embodiments, the collagen Type I may be from bovine or porcine source and may be obtained from either skin (dermal) or tendon.

Bone grafts according to these embodiments may further include at least one further ingredient selected from: 0.2 to 20% by weight hyaluronic acid with respect to the total weight of the bone graft, acid (such as hydrochloric acid) or base (such as sodium hydroxide) in an amount necessary to adjust the pH, which amount may be for example 0.1 to 20% by weight with respect to the total weight of the bone graft, and 20% to 95% by weight DBM.

Further provided herein are methods of making the present bone grafts that include mixing 20% to 95% by weight Collagen Type I with one or more minerals having at least two different dissolution rates or sizes; refrigerating the mixture for 30 minutes to 5 hours; neutralizing the mixture until the pH is between 6.5 and 8.5; refrigerating the mixture for 1 hour to 24 hours; blast chilling the mixture in a freezer at e.g., −40° C., or at least a temperature of less than −20° C., for 1 hour up to 24 hours; freeze drying the mixture for 24 to 72 hours to form a mixture; physically or chemically cross-linking the mixture; and freeze drying the mixture. The method may further include stamping or cutting out the mixture to desired dimensions.

According to non-limiting example embodiments, provided herein are methods of making the present bone grafts that include mixing 20% to 95% by weight Collagen Type I with 0.2 to 20% by weight hyaluronic acid until a desired consistency is reached and obtaining a desired pH of the mixture; refrigerating the mixture for 20 to 72 hours; further mixing to form a homogenous collagen mixture; weighing out at least one of mineral and demineralized bone matrix (an optional extra ingredient); mixing the mineral and optionally DBM with the collagen mixture; refrigerating the mixture for 30 minutes to 5 hours; neutralizing the mixture (e.g., with HCl or NaOH) until the pH is between 6.5 and 8.5; pouring the mixture into a tray; refrigerating the mixture for 1 hour to 24 hours; blast chilling the mixture in a freezer at a temperature of less than or equal to −20° C. for 1 hour up to 24 hours; freeze drying the mixture for 24 to 72 hours to form a mixture; physically or chemically cross-linking the mixture; freeze drying the mixture; and stamping or cutting out the mixture to desired dimensions.

The mineral of these embodiments may include for example, one or more of the following: beta-tricalcium phosphate (size ranging from 75 nm to 500 μm), carbonate apatite (size ranging from 75 nm to 500 μm), and calcium carbonate (size ranging from 75 nm to 500 μm). Thus, example embodiments include collagen Type I and one or more different types of minerals, and/or one or more sizes.

According to example embodiments, the total weight percent of mineral in the bone graft is from 20% to 95% by weight with respect to the total weight of the bone graft.

According to non-limiting example embodiments, the total weight percent of DBM in the bone graft may be from 20% to 95% by weight with respect to the total weight of the bone graft.

Non-limiting example methods according to the present invention are depicted for example, in the flow chart of FIG. 1. As shown in FIG. 1, in example embodiments, collagen is first mixed with HCl. As indicated above, these ingredients may be mixed until a desired consistency is reached. Although not specifically set forth in the flow chart of FIG. 1, a desired pH of the mixture may then be reached. The mixture may then be refrigerated and allowed to swell for up to 20 hours. According to these embodiments, an optional ingredient of DBM is added and the mixture is mixed/homogenized e.g., by mixing in a shear mixer at a speed of 1000 rpm for about 5 minutes. The mineral component is then added to the mixture and again mixed. The mixing may be again be achieved, e.g., by mixing in a shear mixer, e.g., at 500 rpm for 2 minutes. The mixture in these embodiments may then be frozen at a temperature of −40° C. for 12 hours; and the mixture may be freeze dried e.g., for 48 hours.

Methods of Use

Also provided herein are methods that include inserting any of the present bone grafts into a mammal in need of the bone graft. By way of example, the present bone grafts may be inserted into or administered to a mammal by surgically inserting one or more of the present bone grafts into a mammal, such as a mammal, in need thereof. The bone grafts may be inserted or administered for example by themselves e.g., in the form of a strip, putty, gel and/or sponge, or the bone graft may be available in conjunction with an implant, such as being incorporated therein or thereon (e.g., as a coating). The bone grafts may be inserted in an effective amount, as can be determined by a physician taking into account the need for the bone graft, the type of bone graft, and the patient.

As previously indicated, the subject/patient may be a mammal (as well as other animals), and the mammal may be (but does not have to be) human.

Embodiments of the present invention may include moldable and shapeable putty compositions that may be used for example to fill bone defects. Thus, according to example embodiments the present bone grafts may be for example in the form of a putty or other semi-solid or solid form, including, but not limited to, strip, putty, gel or sponge.

Implants

Yet further example embodiments are directed to implants or other devices or products that include one more of the bone grafts provided herein, incorporated into, or on the implant, or otherwise used with the product or implant. For example, the present bone graft substitutes may be used as a graft within or inside an implant. By way of non-limiting example, bone grafts may be used in conjunction with interbody spacers for treatment of compression fractures.

Surgical implants and compositions should be biocompatible to successfully perform their intended function. Biocompatibility may be defined as the characteristic of an implant or composition acting in such a way as to allow its therapeutic function to be manifested without secondary adverse affects such as toxicity, foreign body reaction or cellular disruption. To help avoid adverse reaction, example bone grafts may be prepared in sterile environments and formulations for implantation into a mammal.

Kits

Yet further embodiments are directed to kits that include one or more of the present bone grafts or one or more components or ingredients thereof.

Example kits may include for example, any of the present bone grafts, along with instructions and/or at least one additional component (such as devices, implants, tools) that may be used for example in the storage, preparation or use of the bone graft substitutes. By way of example, the kit components may be used to assist in adding the bone graft to a device or implant, or to assist in inserting the bone graft into a mammal. Further non-limiting examples may include one or more of the present bone grafts and instructions for the preparation of the bone graft, instructions for the use of the bone graft, a tool for insertion of the bone graft into a mammal, a tool or vehicle for hydration of a dry form of the bone graft, and/or an implant to be inserted into the mammal with the bone graft. For example, the bone graft may be provided in a syringe for reconstitution and/or administration to a mammal/patient. According to example embodiments, products may be provided in a syringe with an attachment to deliver product in a minimally invasive manner. Other possible ingredients in kits may include disposal implements or treatment literature.

Yet further non-limiting examples may include one or more ingredients of the present bone grafts, which may be combined, mixed or treated to prepare the present bone grafts. By way of example, the present kits may include collagen Type 1, one or more minerals, and/or other required or optional ingredients of the present bone grafts, which may be combined, mixed or treated in order to form the present bone grafts. Further provided may be instructions for preparation of one or more of the present bone grafts and/or one or more tools, devices, implants, and/or other components to assist in making or using the present bone grafts.

The following examples are provided to further illustrate various non-limiting embodiments and techniques. It should be understood, however, that these examples are meant to be illustrative and do not limit the scope of the claims. As would be apparent to skilled artisans, many variations and modifications are intended to be encompassed within the spirit and scope of the invention.

EXAMPLES

Example 1

According to non-limiting example embodiments, bone grafts are prepared which include collagen type I and one or more different types of mineral, having one or more different rates of dissolution and/or having one or more sizes. The method includes the following:

(1) collagen type I from bovine or porcine source is obtained from either skin (dermal) or tendon.

(2) 20% to 95% Collagen Type 1 (by weight) is mixed with hyaluronic acid (0.2 to 20% by weight) and mixed in a beaker until the desired consistency is reached. Acid (such as HCl) or a base (such as NaOH) can be added to the mixture until a homogenous mixture and desired pH is produced. The pH of the mixture can be for example, between 2.0 and 6.0. (3) Cover mixture and place into refrigerator for 20 to 72 hours.

(4) After refrigerating the mixture (step 3) use a shear mixture to further mix to fully combine into a homogenous mixture (5) Weigh out mineral(s) (such as calcium phosphate, carbonate apatite, and/or calcium carbonate) and/or demineralized bone matrix a) Mineral can include for example, any of the following:
      in combination or alone:

Beta-tricalcium phosphate (size ranging from 75 nm to 500 μm), carbonate apatite (size ranging from 75 nm to 500 μm), and calcium carbonate (size ranging from 75 nm to 500 μm).

b) The total weight percent of minerals in the bone graft can range from 20% to 95% c) The total weight percent of DBM in the bone graft can range from 20% to 95%.

(6) Add mineral(s) to the collagen mixture or vice versa. The mixture can be with or without hyaluronic acid.

(7) Mix using a shear mixer.

(8) Place mixture in a refrigerator for 30 minutes to 5 hours.

(9) Remove the mixture from refrigerator.

(10) Neutralize mixture with an acid such as HCl or with a base such as NaOH until the pH is between 6.5 and 8.5.

(11) Pour the mixture into a tray; the tray material can be metal or polymer-based.

(12) The mixture, once in the tray, can be spread using a metal sheet press.

(13) Cover mixture and place into refrigerator for 1 hour to 24 hours.

(14) Blast chill mixture in the freezer at −40° C. (or at least a temperature of less than −20° C.) for 1 hour up to 24 hours.

(15) Freeze dry mixture for 24 to 72 hours to form a "dried pad" mixture.

(16) Take dried pad mixture and cross link; either chemical or physical methods of cross linking may be used.

(17) Rinse the pad if used a chemical cross linking method.

(18) Freeze dry.

(19) Stamp/cut out to desired dimensions.

In the foregoing specification, the invention has been described with reference to specific embodiments thereof. It will, however, be evident that various modifications and changes may be made thereto without departing from the broader spirit and scope of the invention. Accordingly, it is intended that such changes and modifications fall within the scope of the present invention as defined by the claims appended hereto. The specification and drawings are, accordingly, to be regarded in an illustrative rather than restrictive sense.

We claim:

1. A method of making a bone graft, the method comprising:
   mixing 20% to 95% by weight collagen type I with at least one mineral to form a mixture;
   refrigerating the mixture for 30 minutes to 5 hours to form a cooled mixture;
   neutralizing the cooled mixture to a pH between 6.5 and 8.5 to form a neutralized mixture;
   refrigerating the neutralized mixture for 1 hour to 24 hours to form a cooled, neutralized mixture;
   blast chilling the cooled, neutralized mixture at a temperature below −20° C. for 1 hour up to 24 hours to form a blast chilled mixture;
   freeze drying the blast chilled mixture for 24 to 72 hours to form a dried pad mixture;
   physically or chemically cross-linking the dried pad mixture to form a cross-linked mixture; and
   freeze drying the cross-linked mixture to obtain the bone graft,
   the bone graft comprising 20% to 95% by weight with respect to total weight of the bone graft, of the collagen type I, and 20% to 95% by weight with respect to the total weight of the bone graft, of the at least one mineral, wherein the at least one mineral has two or more different dissolution rates, thereby allowing the bone graft to enhance bone healing in both early and late phases of the bone healing.

2. The method of claim 1, wherein the neutralizing is achieved by adding HCl or NaOH to the cooled mixture.

3. The method of claim 1, wherein the at least one mineral comprises at least one mineral selected from the group consisting of beta-tricalcium phosphate having a size ranging from 75 nm to 500 μm, carbonate apatite having a size ranging from 75 nm to 500 μm, and calcium carbonate having a size ranging from 75 nm to 500 μm.

4. The method of claim 1, wherein the step of mixing the collagen type I with the at least one mineral comprises mixing the collagen type I and the at least one mineral with 20% to 95% by weight of demineralized bone matrix (DBM) with respect to the total weight of the bone graft.

5. The method of claim 1, wherein that at least one mineral mixed with the collagen type I includes a first mineral having a first dissolution profile and a second mineral having a second dissolution profile, wherein the first dissolution profile is different from the second dissolution profile in order to provide for two or more different dissolution rates.

6. The method of claim 5, wherein the first dissolution profile is slower than the second dissolution profile.

7. The method of claim 5, wherein one of the first mineral or the second mineral has a porous structure.

8. The method of claim 1, wherein before mixing the collagen type I with the at least one mineral, the collagen is mixed with 0.2 to 20% by weight of hyaluronic acid with respect to the total weight of the bone graft, and optionally, an additional acid or base in an amount of 0.1 to 20% by weight.

9. The method of claim 1, wherein the collagen type I is from a bovine or porcine source and is obtained from dermal, tendon, or both.

10. A method of making a bone graft, the method comprising:
    mixing 20% to 95% by weight collagen type I with respect to total weight of the bone graft, with 0.2 to 20% by weight hyaluronic acid to form a mixture until a desired consistency is reached and a desired pH of the mixture is obtained;
    refrigerating the mixture for 20 to 72 hours to form a swelled mixture;
    further mixing the swelled mixture to form a homogenous collagen mixture;
    weighing out at least one mineral and demineralized bone matrix (DBM);
    mixing the at least one mineral and DBM with the homogenous collagen mixture to form a mineral-containing collagen mixture;
    refrigerating the mineral-containing collagen mixture for 30 minutes to 5 hours to form a cooled mixture;
    neutralizing the cooled mixture to a pH between 6.5 and 8.5 to form a neutralized mixture;
    refrigerating the neutralized mixture for 1 hour to 24 hours to form a cooled, neutralized mixture;
    blast chilling the cooled, neutralized mixture in a freezer at −20° C. or below for 1 hour up to 24 hours to form a blast chilled mixture;
    freeze drying the blast chilled mixture for 24 to 72 hours to form a dried pad mixture;

physically or chemically cross-linking the dried pad mixture to form a cross-linked mixture; and freeze drying the cross-linked mixture to obtain the bone graft.

11. The method of claim 10, further comprising stamping or cutting out the bone graft to desired dimensions.

12. The method of claim 10, wherein the total weight percent of DBM in the bone graft is from 20% to 95%.

13. A method of making a bone graft, the method comprising:

mixing collagen type I with hyaluronic acid to form a mixture;

refrigerating the mixture for 20 to 72 hours to form a swelled mixture;

mixing the swelled mixture to form a homogenous collagen mixture;

adding a first mineral having a first dissolution profile and a second mineral having a second dissolution profile and mixing with the homogenous collagen mixture to form a mineral-containing collagen mixture, wherein the first dissolution profile is different from the second dissolution profile;

refrigerating the mineral-containing collagen mixture for 30 minutes to 5 hours to form a cooled mixture;

neutralizing the cooled mixture to a pH between 6.5 and 8.5 to form a neutralized mixture;

refrigerating the neutralized mixture for 1 hour to 24 hours to form a cooled, neutralized mixture;

blast chilling the cooled, neutralized mixture in a freezer at −20° C. or below for 1 hour up to 24 hours to form a blast chilled mixture;

freeze drying the blast chilled mixture for 24 to 72 hours to form a dried pad mixture;

physically or chemically cross-linking the dried pad mixture to form a cross-linked mixture; and freeze drying the cross-linked mixture to obtain the bone graft.

14. The method of claim 13, wherein the first dissolution profile is slower than the second dissolution profile.

15. The method of claim 14, wherein the first mineral with the first dissolution profile has a porous structure.

16. The method of claim 13, further comprising adding demineralized bone matrix (DBM) with the first and second minerals when forming the mineral-containing collagen mixture.

* * * * *